US00PP14678P29

(12) United States Plant Patent
Noodelijk

(10) Patent No.: US PP14,678 P2
(45) Date of Patent: Apr. 6, 2004

(54) CHRYSANTHEMUM PLANT NAMED 'MARS'

(50) Latin Name: *Chrysanthemum morifolium*
Varietal Denomination: Mars

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 86 days.

(21) Appl. No.: 10/316,865

(22) Filed: Dec. 12, 2002

(51) Int. Cl.[7] ..... A01H 5/00
(52) U.S. Cl. ..... Plt./286
(58) Field of Search ..... Plt./286

*Primary Examiner*—Anne Marie Grunberg
(74) *Attorney, Agent, or Firm*—Parkhurst & Wendel, L.L.P.

(57) ABSTRACT

A chrysanthemum plant named 'Mars' characterized by its medium sized blooms with yellow ray florets and prolific branching; natural season flower date September 9–16; blooming for a period of 5 weeks.

3 Drawing Sheets

BACKGROUND OF THE INVENTION

'Mars' is a product of a breeding and selection program for outdoor pot mums (garden mums) which had the objective of creating new chrysanthemum cultivars with a daisy type flower, a natural season flower date around September 9–16; blooming for a period of 5 weeks. The new plant of the present invention comprises a new and distinct cultivar of Chrysanthemum plant 'Mars' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout Holland in September 2000. The plant has been asexually reproduced by cuttings in greenhouses at Rijsenhout Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
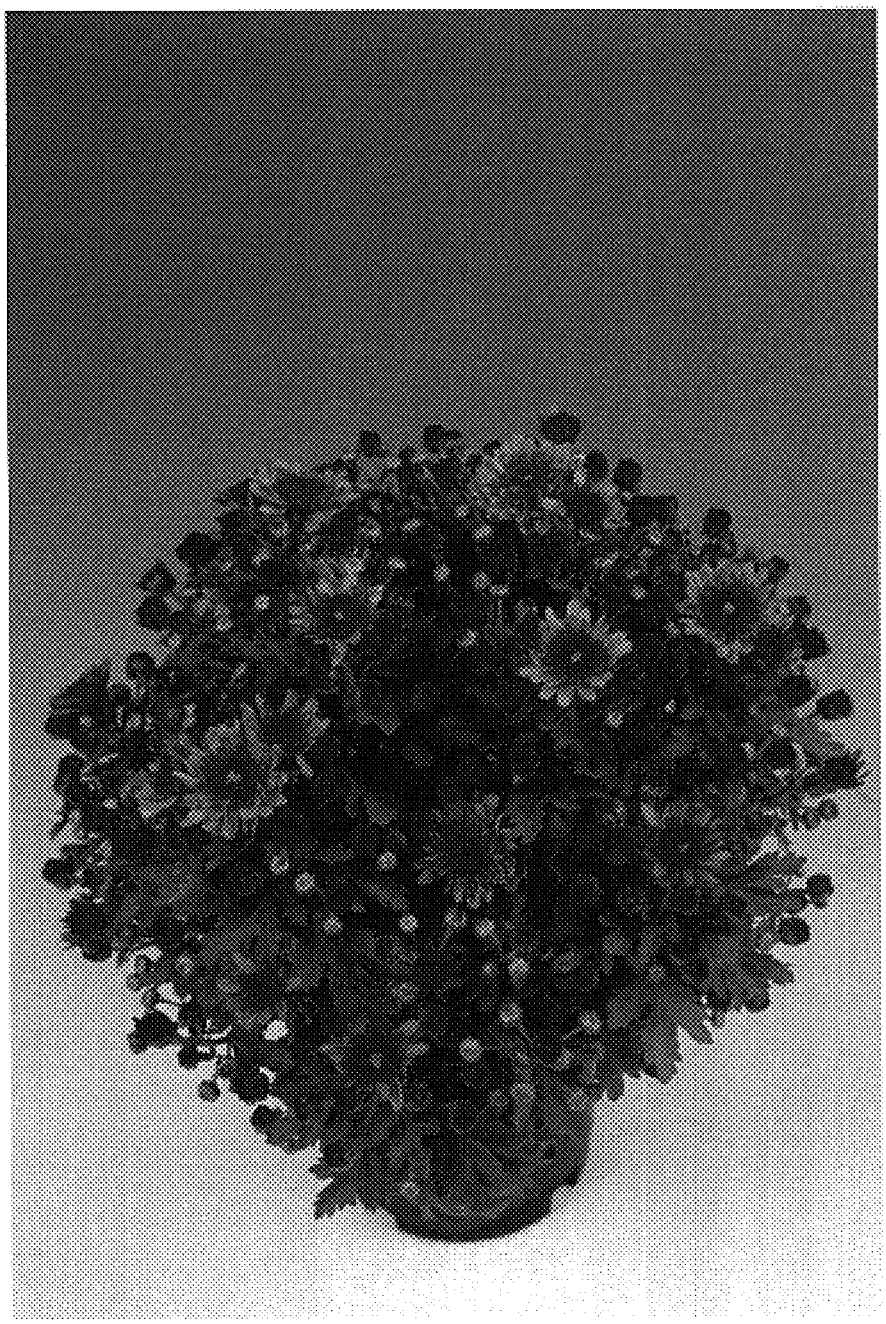
FIG. 1 shows a plant of the cultivar in full bloom.
Figure 2:
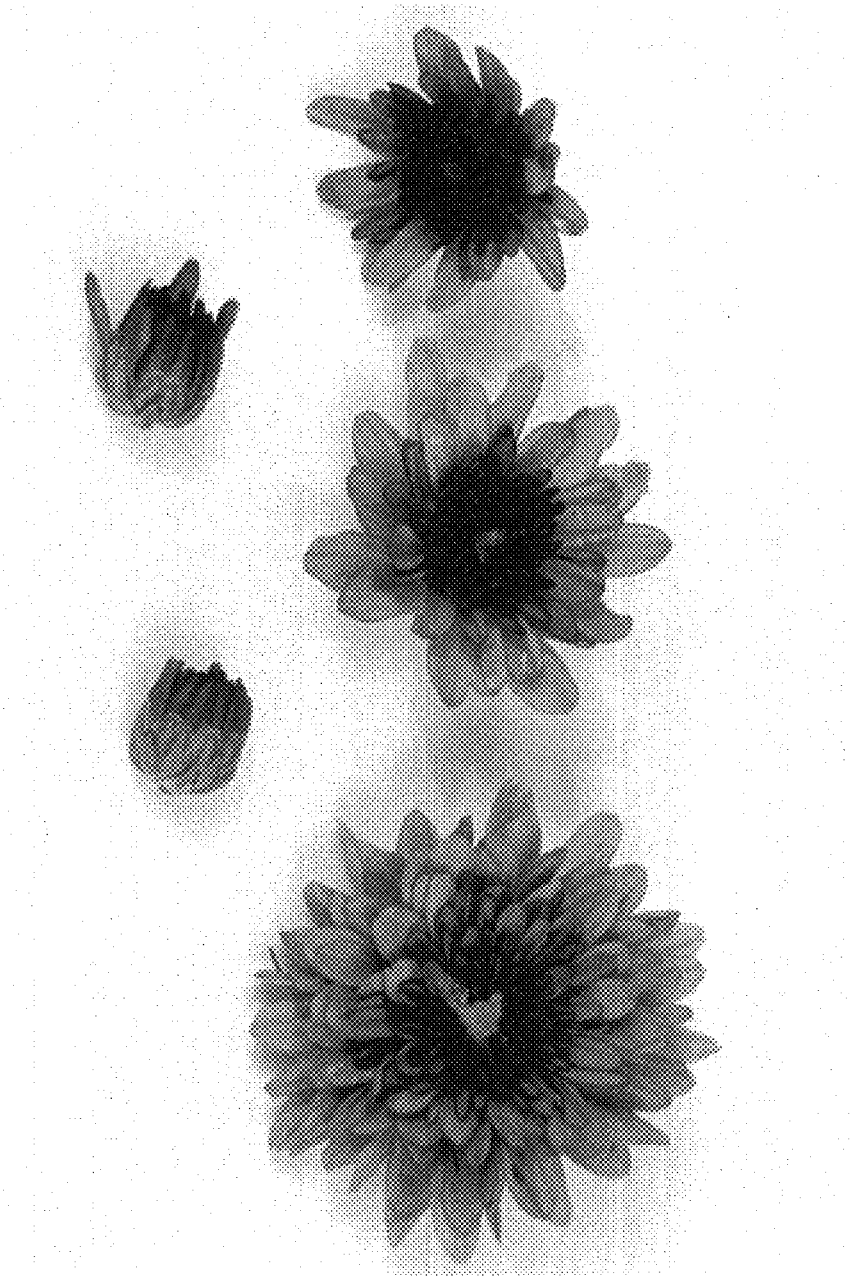
FIG. 2 shows the various stages of bloom of the new cultivar.
Figure 3:
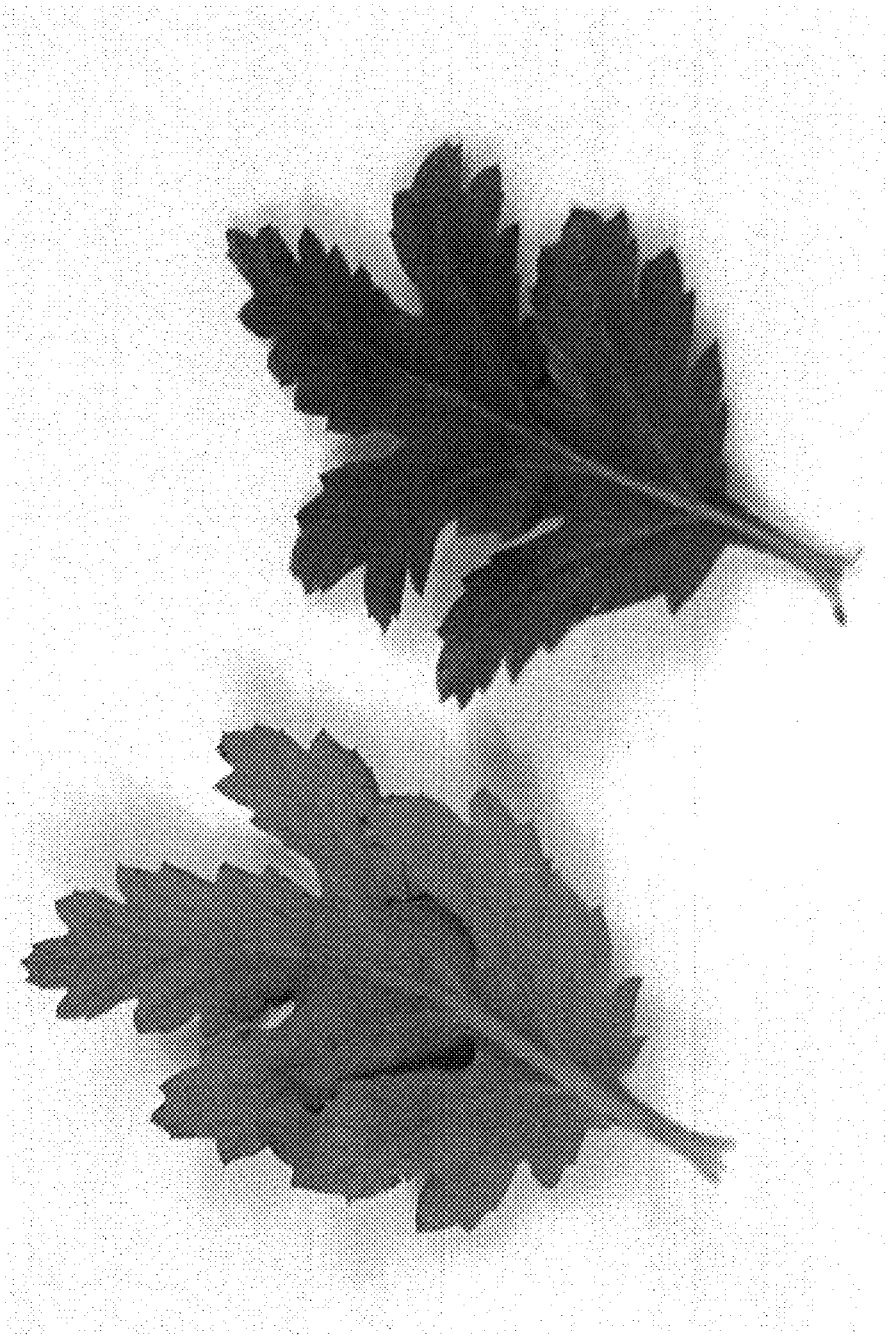
FIG. 3 shows the petiole and foliage of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 2000 and 2001. The natural blooming date of this crop was September 9–16 (week 37). The average height of the plants was 23 cms. No growth retardants were used. No tests were done on disease or insect resistance or susceptibility. No tests were done on cold or drought tolerance. This new variety produces medium sized blooms with yellow ray florets and a red center blooming for a period of 5 weeks.

From the cultivars known to inventor the most similar existing cultivar in comparison to 'Mars' is 'Iduna' (U.S. Plant patent application Ser. No. 10/316,869). When 'Iduna' and 'Mars' are being compared the following differences are noticed: The differences of 'Iduna' and 'Mars' are (1) Flowerform. Both 'Mars' and 'Iduna' have two-tone decorative flowers with a very dark colored center. The difference is the presence of disc-florets: in 'Mars' disc-florets are present when mature. (2) Natural flowering date. 'Mars' flowers much later than 'Iduna'.

The following is a description of the plant and characteristics that distinguish 'Mars' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1. Botanical Description of Cultivar 'Mars'

Bud:
- *Size.*—Medium ;cross-section 1.0 cm, height 1.2 cm.
- *Outside color.*—Greyed-red 179 A.
- *Involucral bracts.*—2 rows, length 7 mm, width 3 mm.
- *Involucral bracts among disc-florets.*—Not present.
- *Involucral bracts color.*—Green 138 A.

Bloom:
- *Type.*—Daisy.
- *Height.*—Flat. 1 cm.
- *Size.*—Medium.
- *Fully expanded.*—4.5–5.0 cm.
- *Number of blooms per branch.*—Approx. 5–7 blooms per branch.
- *Performance on the plant.*—5 weeks.
- *Seeds.*—Produced in large quantities, ovate grey-brown 199A, 1½ mm in length.
- *Fragrance.*—Typical chrysanthemum, slightly.

Color:
- *Center of the flower (disc florets when mature).*—Immature greyed-red 179 A. Mature yellow-orange 15 A.
- *Color of upper surface of the ray-florets.*—Yellow-orange 22 B.

*Color of the lower surface of the ray-florets.*—Yellow-orange 22B.
*Tonality from distance.*—A garden mum with yellow flowers and a red disc.
*Color the upper surface of the ray-florets after aging of the plant.*—Yellow-orange 22 B for the outer part and yellow-orange 15A for the inner part.

Ray florets:
*Texture.*—Upper and under side smooth.
*Number.*—130–140.
*Cross-section.*—Twisted.
*Longitudinal axis of majority.*—Straight.
*Length of corolla tube.*—0.3 cm.
*Ray-floret margin.*—Entire.
*Ray-floret length.*—2.0 cm.
*Ray-floret width.*—0.5 cm.
*Ratio length/width.*—Medium.
*Shape of tip.*—Rounded.
*Disc florets.*—Present.
*Disc diameter.*—0.5 cm.
*Distribution of disc florets.*—Numerous, visible when mature.
*Shape.*—Tubular.
*Color.*—Yellow-orange 15A.
*Receptacle shape.*—Conical raised.

Reproductive organs:
*Stamen* (*present in disc florets only*).—Thin, 3 mm in length.
*Stamen color.*—Yellow green 144 A.
*Pollen.*—Present in small amount.
*Pollen color.*—Yellow 7 A.
*Styles.*—Thin.
*Style color.*—Yellow-green 144 A.
*Style length.*—4 mm.
*Stigma color.*—Yellow-green 144 A.
*Stigma width.*—1 mm.
*Ovaries.*—Enclosed in calyx.

Plant:
*Shape.*—Grown as a spray-type pot mum, outdoor mounded and round.
*Growth habit.*—Spreading.
*Growth rate.*—Slow.
*Height.*—23 cm.
*Width.*—32–34 cm.
*Stem color.*—Yellow-green 148 B.
*Stem strength.*—Strong.
*Stem brittleness.*—Present.
*Stem anthocyanin coloration.*—Absent.
*Length of lateral branch.*—From top to bottom 11–12 cm.
*Lateral branch color.*—Yellow-green 148 B.
*Lateral branch, attachment.*—Brittle.
*Branching* (*average number of lateral branches*).—Good with 6–7 breaks after pinching.
*Peduncle length.*—3.0 cm.
*Peduncle color.*—Yellow-green 148B .
*Natural season blooming date.*—September 9–16.

Foliage:
*Color.*—Upper side yellow-green 148 B. Under side yellow-green 148 C.
*Size.*—Medium.; length 7.0 cm, width 5.0 cm.
*Quantity* (*number per lateral branch*).—7–9.
*Shape.*—Elliptic.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Round.
*Margin of sinus between lateral lobes.*—Converging.
*Shape of base.*—Rounded.
*Apex.*—Mucronate.

TABLE 2

Differences with the comparisons varieties

| | 'MARS' | 'IDUNA' |
|---|---|---|
| Color of the center of the immature flower | Grey-red 179 A | Greyed-red 179 A |
| Color of the center of the mature flower | Yellow-orange 15 A | Greyed-red 179 A |
| Natural flowering date | September 9–16 | August 12–17 |

I claim:

1. A new and distinct variety of chrysanthemum plant as described and illustrated.

* * * * *